US012599365B2

(12) United States Patent

Schmidt et al.

(10) Patent No.: US 12,599,365 B2
(45) Date of Patent: Apr. 14, 2026

(54) STABILIZING TRANSNASAL BALLOON SHEATH

(71) Applicant: Medtronic, Inc., Minneapolis, MN (US)

(72) Inventors: Elliot C. Schmidt, Minneapolis, MN (US); Kristin M. Johnson, Circle Pines, MN (US)

(73) Assignee: Medtronic, Inc., Minneapolis, MN (US)

( * ) Notice: Subject to any disclaimer, the term of this patent is extended or adjusted under 35 U.S.C. 154(b) by 1219 days.

(21) Appl. No.: 17/500,738

(22) Filed: Oct. 13, 2021

(65) Prior Publication Data

US 2022/0117577 A1 Apr. 21, 2022

Related U.S. Application Data

(60) Provisional application No. 63/092,332, filed on Oct. 15, 2020.

(51) Int. Cl.
*A61B 8/00* (2006.01)
*A61B 1/00* (2006.01)
(Continued)

(52) U.S. Cl.
CPC .......... *A61B 8/445* (2013.01); *A61B 1/00082* (2013.01); *A61B 8/0883* (2013.01);
(Continued)

(58) Field of Classification Search
CPC ......... A61B 8/445; A61B 8/0883; A61B 8/12; A61B 8/54; A61B 17/3468; A61B 8/0833;
(Continued)

(56) References Cited

U.S. PATENT DOCUMENTS 4,721,097 A * 1/1988 D'Amelio ............ A61B 1/0055
600/128
4,973,321 A * 11/1990 Michelson ............. A61B 1/317
600/114
(Continued)

FOREIGN PATENT DOCUMENTS

WO 199321816 A1 11/1993
WO 2015/057533 A1 4/2015
WO WO-2020146889 A1 * 7/2020 ....... A61B 17/00234

OTHER PUBLICATIONS

International Search Report and Written Opinion of International Application No. PCT/US2021/054961, dated Feb. 25, 2022, 16 pp.
(Continued)

*Primary Examiner* — Nathan R Price
(74) *Attorney, Agent, or Firm* — Shumaker & Sieffert, P.A.

(57) ABSTRACT

A transnasal transesophageal balloon catheter includes at least one compliant balloon attached to the external surface of the tubular body. An arrangement of structures extend away from the internal surface of the tubular body, and exposed probe guide surfaces on the structures form a lumen with a diameter of less than about 15 French (Fr) (5 mm) extending from the proximal end to the distal end of the tubular body and configured to slidably and rotatably receive the ultrasound probe. An arrangement of elongate fluid channels are interspersed with the structures. The fluid channels are in fluid communication with the lumen and transport a fluid between a fluid ingress port and a fluid egress port to at least partially inflate or deflate the balloon.

15 Claims, 8 Drawing Sheets

(51) Int. Cl.

| | |
|---|---|
| *A61B 8/08* | (2006.01) |
| *A61M 25/00* | (2006.01) |
| *A61M 25/10* | (2013.01) |
| *A61B 8/12* | (2006.01) |
| *A61B 17/34* | (2006.01) |
| *A61M 25/02* | (2006.01) |

(52) U.S. Cl.
CPC .... *A61M 25/0023* (2013.01); *A61M 25/0032* (2013.01); *A61M 25/0082* (2013.01); *A61M 25/10* (2013.01); *A61M 25/1002* (2013.01); *A61B 8/12* (2013.01); *A61B 8/54* (2013.01); *A61B 17/3468* (2013.01); *A61M 2025/0004* (2013.01); *A61M 25/001* (2013.01); *A61M 25/0014* (2013.01); *A61M 25/0015* (2013.01); *A61M 25/0067* (2013.01); *A61M 2025/022* (2013.01); *A61M 2025/0226* (2013.01); *A61M 25/1011* (2013.01); *A61M 2025/1043* (2013.01); *A61M 2025/1068* (2013.01)

(58) Field of Classification Search
CPC . A61B 8/4245; A61B 1/2736; A61B 1/00082; A61M 25/0023; A61M 25/0032; A61M 25/0082; A61M 25/10; A61M 25/001; A61M 25/0014; A61M 25/0015; A61M 25/0067; A61M 25/1011; A61M 2025/0004; A61M 2025/022; A61M 2025/0226; A61M 2025/1043; A61M 2025/1068; A61M 25/0029; A61M 25/1002; A61M 2025/1056
USPC ...................................................... 604/164.02
See application file for complete search history.

(56) References Cited

U.S. PATENT DOCUMENTS

| | | | | |
|---|---|---|---|---|
| 5,593,394 | A * | 1/1997 | Kanesaka | A61M 25/0023 604/524 |
| 5,797,882 | A * | 8/1998 | Purdy | A61M 25/0023 604/524 |
| 5,989,183 | A * | 11/1999 | Reisdorf | A61B 1/00135 600/156 |
| 6,827,710 | B1 * | 12/2004 | Mooney | A61B 17/3417 604/43 |
| 7,500,947 | B2 * | 3/2009 | Kucklick | A61B 17/3423 600/128 |
| 8,123,676 | B2 * | 2/2012 | Kucklick | A61B 1/00135 600/128 |
| 8,226,548 | B2 * | 7/2012 | Kucklick | A61B 17/3417 600/128 |
| 8,303,509 | B2 | 11/2012 | Webler et al. | |
| 9,289,575 | B2 * | 3/2016 | Dye | A61M 25/0023 |
| 2003/0004400 | A1 * | 1/2003 | Smith | A61B 1/018 600/153 |
| 2006/0161135 | A1 * | 7/2006 | VanDerWoude | A61M 25/0023 604/524 |
| 2006/0259137 | A1 * | 11/2006 | Artof | A61F 2/243 623/2.11 |
| 2008/0025145 | A1 | 1/2008 | Peszynski et al. | |
| 2014/0276079 | A1 * | 9/2014 | Yamagata | A61B 8/4494 600/459 |
| 2016/0249859 | A1 * | 9/2016 | Babkin | A61B 8/445 600/509 |
| 2016/0287278 | A1 | 10/2016 | Stigall et al. | |
| 2018/0000449 | A1 | 1/2018 | Moore et al. | |
| 2019/0053782 | A1 * | 2/2019 | Stigall | A61B 8/12 |
| 2020/0061339 | A1 * | 2/2020 | Lindenroth | A61B 8/0883 |
| 2020/0139092 | A1 | 5/2020 | Tearney et al. | |

OTHER PUBLICATIONS

Brickner, "Transesophageal Echocardiography," JDMS, Journal of Diagnostic Medical Sonography, vol. 21, No. 4, DOI: 10.1177/8756479305275569, Jul./Aug. 2005, pp. 309-317.

Klettas et al., "Is transnasal TEE imaging a viable alternative to conventional TEE during structural cardiac interventions to avoid general anaesthesia? A pilot comparison study of image quality," Transnasal TEE in cardiac interventions, Journal of Echo Research and Practice, DOI: 10.1530/ERP-16-0029, Mar. 2017, 7 pp.

Stec et al., "First experience with microprobe transoesophageal echocardiography in non-sedated adults undergoing atrial fibrillation ablation: feasibility study and comparison with intracardiac echocardiography," European Society of Cardiology, Europace, vol. 13, doi:10.1093/europace/euq349, Sep. 29, 2010, pp. 51-56.

Szili-Torok et al., "Transnasal transoesophageal ultrasound: the end of the intracardiac echocardiography age?," European Society of Cardiology, Europace, vol. 13, doi:10.1093/europace/euq438, Nov. 4, 2010, pp. 7-8.

Wang et al., "The feasibility study of transnasopharyngeal esophagus echocardiography in the ultrasonic diagnosis," Cardiovascular Ultrasound, vol. 17, No. 4, doi.org/10.1186/s12947-019-0154-2, Mar. 2019, 6 pp.

* cited by examiner

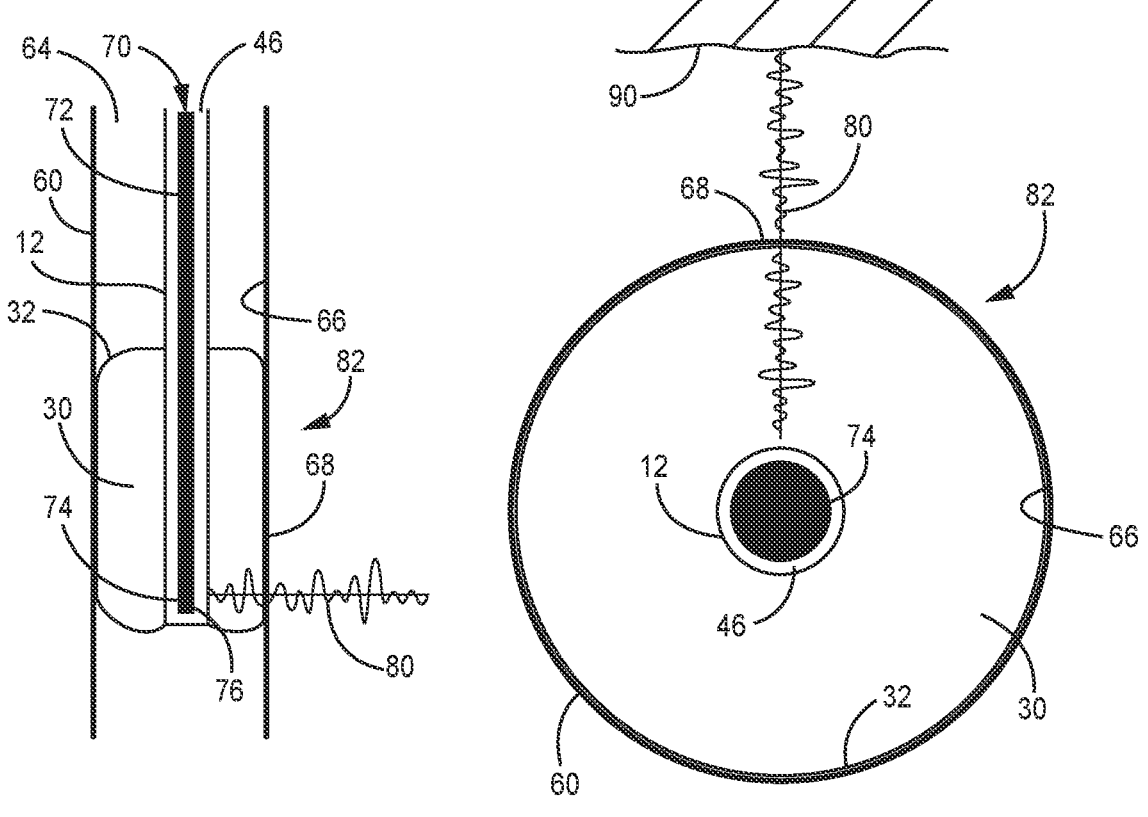
FIG. 3A          FIG. 3B

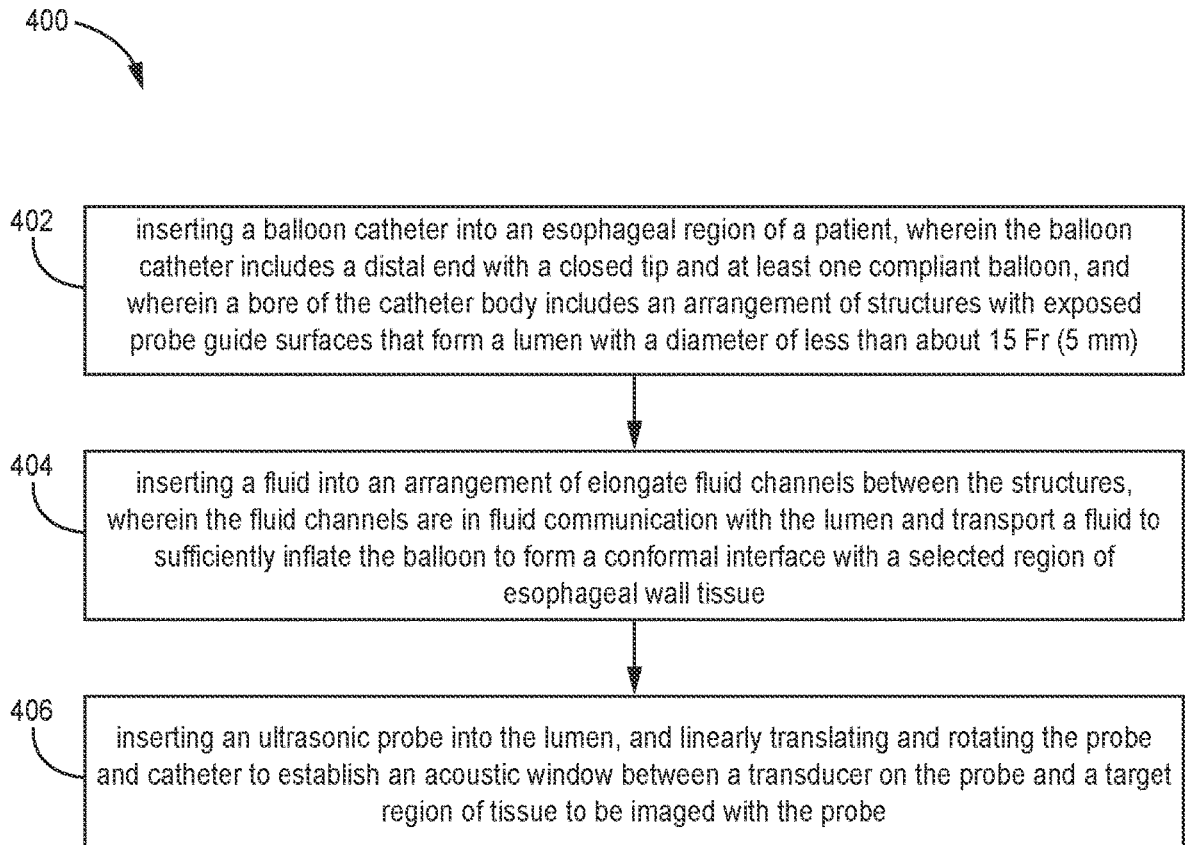

400

402 — inserting a balloon catheter into an esophageal region of a patient, wherein the balloon catheter includes a distal end with a closed tip and at least one compliant balloon, and wherein a bore of the catheter body includes an arrangement of structures with exposed probe guide surfaces that form a lumen with a diameter of less than about 15 Fr (5 mm)

404 — inserting a fluid into an arrangement of elongate fluid channels between the structures, wherein the fluid channels are in fluid communication with the lumen and transport a fluid to sufficiently inflate the balloon to form a conformal interface with a selected region of esophageal wall tissue 406 — inserting an ultrasonic probe into the lumen, and linearly translating and rotating the probe and catheter to establish an acoustic window between a transducer on the probe and a target region of tissue to be imaged with the probe

FIG. 6

STABILIZING TRANSNASAL BALLOON SHEATH

This application claims the benefit of U.S. Provisional Patent Application No. 63/092,332, filed 15 Oct. 2020, the entire contents of which is incorporated herein by reference.

BACKGROUND

Transthoracic echo (TTE) is a relatively inexpensive and less invasive form of ultrasound imaging. However, to provide a good quality image, TTE requires acoustic windows, areas of the anatomy unimpeded by bone and air (lungs), which allow sound to transmit from an ultrasound probe to and from the target tissue. The variability in acoustic windows limits the utility and broad applicability of TTE in, for example, cardiac imaging procedures.

In intracardiac echo (ICE) imaging procedures, a relatively small catheter is advanced through the veins of a patient and the ultrasound transducer is moved through the catheter and placed directly into the heart, which largely eliminates any imaging issues related to patient anatomy. However, ICE utilizes single-use probes that are either discarded or collected and reprocessed after every procedure, which increases costs.

In transesophageal echo (TEE) imaging procedures, the ultrasound probe is positioned in the esophagus of a patient in a region adjacent to the heart, so TEE procedures are less impeded by acoustic windows. However, due to the gag reflex (patients are intubated), high levels of sedation or general anesthesia are typically needed for patient comfort during procedures. Increased anesthesia comes with additional patient risks, as well as procedural costs. In addition, since TEE probes include large, relatively stiff catheters, in some patients the probes may be more likely to cause trauma and additional complications. Further, image quality in TEE procedures can suffer if good contact between the probe and the esophagus wall is not maintained across the full transducer surface. A gap between the transducer and the esophagus wall can introduce air, which can block nearly 100% of sound energy transmission, resulting in significant shadowing in the ultrasound image.

In some cases, TEE imaging can be conducted while guiding the probe into the esophagus through the nose of the patient rather than through the mouth. A goal of this procedure, which has been referred to as transnasal TEE (TNTEE), is to eliminate the gag response associated with the oral pathway, which can in turn reduce or eliminate the need for additional anesthesia and improve patient comfort. TNTEE procedures have been conducted with a pediatric micro TEE probe having rectangular tip dimensions of about a 7.5 mm×5.55 mm, or an average of about 18 French (Fr). TNTEE using a pediatric TEE probe produces images generally comparable to those obtained with traditional TEE.

However, while the probe in TNTEE is smaller than a full-size TEE probe, the micro TEEs are still large relative to the nasal passages of some patients. In some TNTEE procedures, particularly in patients who have previously been prescribed anticoagulants, nose bleeds can occur during probe insertion. In addition, it can be more difficult for a practitioner to maintain contact between the smaller probe and the esophagus or gastric wall, which can produce lower quality images. Further, while the imaging during ICE-guided procedures can be conducted by an implanting physician, TEE and TNTEE often require a dedicated user to operate and position the probe, which can increase the costs and complexity of the procedures.

SUMMARY

In general, the present disclosure is directed to an ultrasonic imaging system including an elongate flexible tubular catheter that improves image quality for transnasal transesophageal echo (TNTEE) imaging procedures. The catheter includes an internal lumen configured to retain a small and maneuverable three-dimensional ultrasonic probe, e.g., suitable for use in intracardiac echo (ICE) imaging procedures. The ICE ultrasonic probe has a diameter of less than about 15 Fr (5 mm), and in some cases can even have a diameter smaller than 10 Fr (3.3 mm). This reduction in catheter size relative to the 18 Fr (6 mm) diameter catheter typically used in TNTEE procedures can provide easy, atraumatic passage through almost all nasal passages of a patient.

In some cases, as noted above, it can be difficult for a practitioner to maintain contact between a smaller diameter ultrasonic probe and the esophageal wall, which can impede the formation of acoustic windows and degrade imaging results.

To form and more readily maintain a more consistent acoustic window and improve TNTEE images of cardiac structures such as, for example, the interatrial septum, the catheter in the imaging system of the present disclosure includes a distal end with a compliant balloon. When inflated with a fluid, the balloon creates a conformal interface with a selected region of esophageal wall tissue, which provides a substantially air-free path between at least one transducer on the ultrasound probe and a target region of tissue to be imaged with the ultrasound probe. The inflated balloon also stabilizes the catheter within the esophagus eliminating the need for an operator to actively stabilize the catheter. In various embodiments, the balloon may have a circular profile to fill symmetrically in the esophagus, or to enhance patient comfort may extend only part of the way around the tubular body of the catheter to allow saliva passage during the imaging procedure.

To more effectively stabilize the small diameter ultrasonic probe within the tubular body of the catheter, an arrangement of structures extending away from an internal surface of the catheter body provides a lumen with probe guide surfaces configured to contact the probe, track with the probe to a selected imaging site within the esophagus, and to rotate with the probe to ensure that one or more transducers on the probe have an unobstructed view of the target tissue to be imaged. The structures on the internal surface of the catheter lumen are interspersed with an arrangement of fluid passages that form a fluid delivery network that delivers fluid to inflate or deflate the balloon and evacuates trapped air without interfering with the movement of the probe within the lumen.

The catheter body has a closed distal end for insertion into the nasogastric region and esophagus of a patient, which can prevent fluid or tissue contamination from contacting the ultrasonic probe, and can likewise prevent the probe materials from contacting the patient. This closed system provides a safety benefit for the patient and in some cases can allow the probes to be reused without extensive re-sterilization, which can reduce the costs of ultrasonic imaging procedures.

In some embodiments, the closed distal end of the catheter can include an atraumatic tip, as no particular shape or torque is required for the tubular catheter body, and in some cases the tip can be tapered to have a dilating effect on the nasal passage. In some cases, a tapered atraumatic tip can reduce nasal bleeds and a lower the complication rate for TNTEE imaging procedures.

In one aspect, the present disclosure is directed to a transnasal transesophageal balloon catheter that includes an elongate flexible tubular body with an internal surface, an external surface, and a bore extending from a proximal end to a distal end thereof. The proximal end of the tubular body includes a valve for introduction of an ultrasound probe and a fluid ingress port, and a distal end of the tubular body comprises a closed tip and a fluid egress port. The fluid egress port is fluidly connected to at least one compliant balloon attached to the external surface of the tubular body, and at least one balloon overlies an imaging region of the tubular body. An arrangement of structures extends away from the internal surface of the tubular body and into the bore, wherein exposed probe guide surfaces on the structures form a lumen with a diameter of less than about 15 French (Fr) (5 mm) extending from the proximal end to the distal end of the tubular body and configured to slidably and rotatably receive the ultrasound probe. An arrangement of elongate fluid channels are interspersed with the structures, wherein the fluid channels are in fluid communication with the lumen and transport a fluid between the fluid ingress port and the fluid egress port to at least partially inflate or deflate the balloon.

In another aspect, the present disclosure is directed to a system including a balloon catheter. The balloon catheter includes an elongate flexible tubular body with an internal surface, an external surface, and an open bore extending from a proximal end to a distal end thereof, wherein the proximal end of the tubular body includes a valve configured to sealably accept an ultrasound probe and a fluid ingress port. A distal end of the tubular body includes a closed tip and a fluid egress port, wherein the fluid egress port is fluidly connected to at least one compliant balloon attached to the external surface of the tubular body, and wherein the at least one balloon overlies an imaging region of the tubular body. An arrangement of structures extends away from the internal surface of the tubular body and into the bore, wherein exposed probe guide surfaces on the structures form a lumen with a diameter of less than about 15 Fr (5 mm) extending from the proximal end to the distal end of the tubular body and configured to slidably receive the ultrasound probe. An arrangement of elongate fluid channels reside between the structures, wherein the fluid channels are in fluid communication with lumen and transport a fluid between the fluid ingress port and the fluid egress port to at least partially inflate or deflate the balloon in the imaging region. An intracardiac echo probe is in the lumen, and is linearly translatable and rotatable in the lumen.

In another aspect, the present disclosure is directed to a method for ultrasonic imaging a target tissue. The method incudes inserting a balloon catheter into an esophageal region, wherein the balloon catheter includes an elongate flexible tubular body with an internal surface, an external surface, and an open bore extending from a proximal end to a distal end thereof. The proximal end of the tubular body includes a valve configured for sealable introduction of an intracardiac echo probe and a fluid ingress port, and a distal end of the tubular body includes a closed tip and a fluid egress port. The fluid egress port is fluidly connected to at least one compliant balloon attached to the external surface of the tubular body, and wherein the at least one balloon overlies an imaging region of the tubular body. An arrangement of structures extends away from the internal surface of the tubular body and into the bore, wherein exposed probe guide surfaces on the structures form a lumen with a diameter of less than about 15 Fr (5 mm) extending from the proximal end to the distal end of the tubular body and configured to slidably and rotatably receive the probe. An arrangement of elongate fluid channels resides between the structures, wherein the fluid channels are in fluid communication with lumen and transport a fluid between the fluid ingress port and the fluid egress. The method includes linearly translating and rotating the balloon catheter to a selected region of esophageal wall tissue, and inserting a fluid into the fluid ingress port such that the fluid enters the fluid channels and the lumen and flows from the liquid egress port to sufficiently inflate the balloon in the imaging region to form a conformal interface with the selected region.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 3A-3B are schematic diagrams of imaging systems with catheters of the present disclosure in an esophagus of a patient.

FIG. 6 is a flow chart of an illustrative embodiment of an ultrasonic imaging method including the imaging system of FIG. 5.

Like symbols in the drawings indicate like elements.

DETAILED DESCRIPTION

Figure 1:
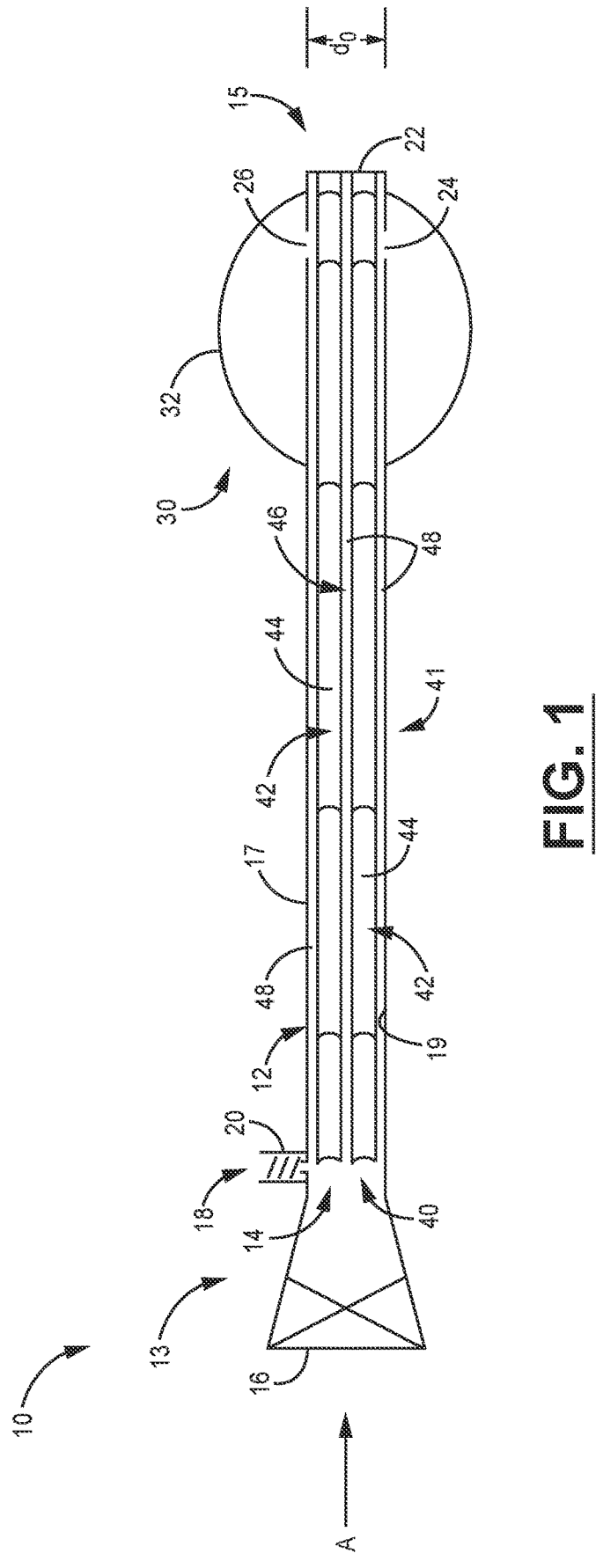
FIG. 1 is schematic cross-sectional side view of an embodiment of a catheter according to the present disclosure.

FIG. 1 is a schematic illustration (which is not to scale) of a catheter 10 for stabilizing and guiding an ultrasonic imaging probe in an imaging system suitable for use in performing transnasal transesophageal echo (TNTEE) imaging procedures. The catheter 10 includes an elongate flexible tubular body 12 with a proximal end 13 and a distal end 15. The catheter body 12 can be made of any flexible material, and is generally formed by extrusion of a polymeric material including, but not limited to, polyethylene (PE), nylon, polypropylene (PP), polyether block amide (PEBA), polybutylene terephthalate (PBT) and combinations thereof. In various embodiments, the catheter body 12 can be formed from a single layer of polymeric material, or multiple layers of the same or different polymeric materials. In some examples, which are not intended to be limiting, the catheter body 12 can have an outside diameter do of about 12 Fr (4 mm) to about 25 Fr (8.3 mm) for a transesophageal catheter that can be delivered transnasally. In some embodiments, the catheter body can optionally include a reinforcing material such as, for example, metal strands, ribbons, wires and the like (not shown in FIG. 1).

In various embodiments, the distal end 15 of the catheter body 12 can be straight as shown in FIG. 1, or may be tapered. The catheter body 12 includes an exterior surface 17, an interior surface 19, and an open longitudinal bore 14 extending along its length from the proximal end 13 to the distal end 15 thereof.

The proximal end 13 of the catheter body 12 includes a valve 16 suitable for introduction of an ultrasonic imaging probe apparatus such as a TNTEE transducer and shaft (not shown in FIG. 1, will be shown in more detail below). The valve 16 may vary widely, and should be configured to include a sealing member such as, for example, a O-ring, gasket, sealable septum, and the like that accepts the TNTEE transducer and shaft, and then forms a liquid-tight seal with the TNTEE probe shaft that prohibits liquid from passing therethrough. The proximal end 13 of the catheter body 12 also includes a fluid ingress port 18. In some example embodiments, the fluid ingress port 18 includes a luer lock connector 20, but any type of connector may potentially be used to connect the catheter body 12 to a source of fluid. In some embodiments, the catheter body may include a plurality of fluid ingress ports 18.

The distal end 15 of the catheter body 12 includes a closed tip 22 that seals the catheter body 12 to prevent fluid leakage and prevent contact between the ultrasound probe therein and bodily fluids of the patient. In the embodiment of FIG. 1, the tip 22 is integral with the catheter body 12, but in some embodiments the tip 22 may be made from an atraumatic polymeric material that is, for example, softer and more compliant than the polymeric material used to form the catheter body 12. In some embodiments, the tip 22 may be tapered to provide a dilating effect and ease passage of the tip 22 through the nasal passages and esophagus of a patient. The distal end 15 of the catheter body 12 further includes at least one fluid egress port, and in the embodiment of FIG. 1 includes dual fluid egress ports 24, 26. However, in some examples the catheter body 12 can include multiple lumens and channels, each with multiple fluid egress ports.

The distal end 15 of the catheter body 12 further includes at least one compliant balloon 30 that overlies the fluid egress ports 24, 26. In some example embodiments, which are not intended to be limiting, the balloon 30 is formed from a soft, flexible, compliant polymeric material such as, for example polyethylene (PE)/ethylene vinyl alcohol (EVA) blends, silicone, polyurethane, polyether block amide, and combinations thereof. The balloon 30 includes a balloon wall 32 that may be formed from a single layer or multiple layers of polymeric materials, and may optionally include reinforcing materials to enhance strength and burst resistance. In some example embodiments, the balloon 30 has a length along the catheter body 12 of about 2 cm to about 10 cm. The balloon wall 32 can be attached to the external surface 17 of the catheter body 12 by any suitable technique including, for example, bonding, fusing, and the like.

Figure 2A:
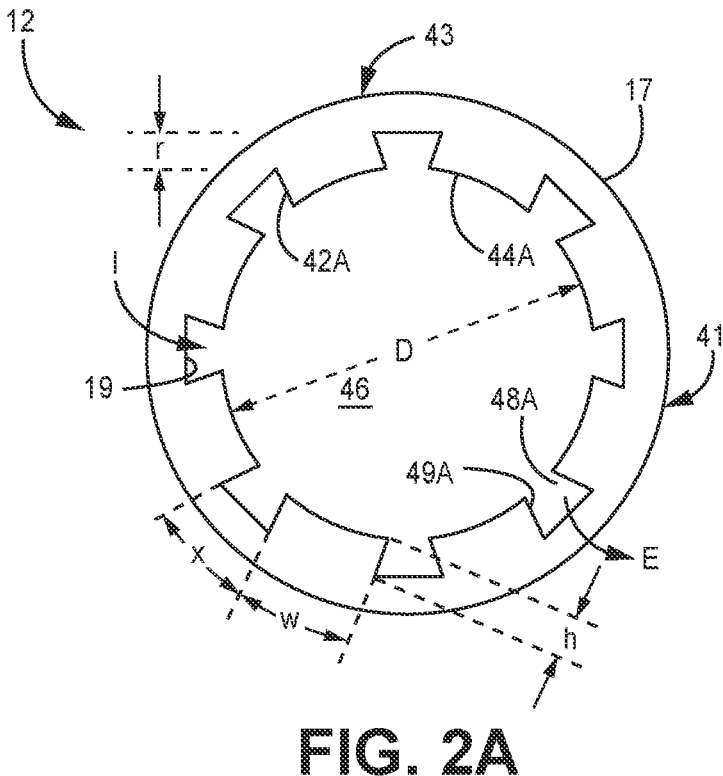
FIGS. 2A-2B are schematic cross-sectional views along the direction of arrow A of FIG. 1 of embodiments of structures and fluid flow channels in the catheter of FIG. 1.
Figure 2B:
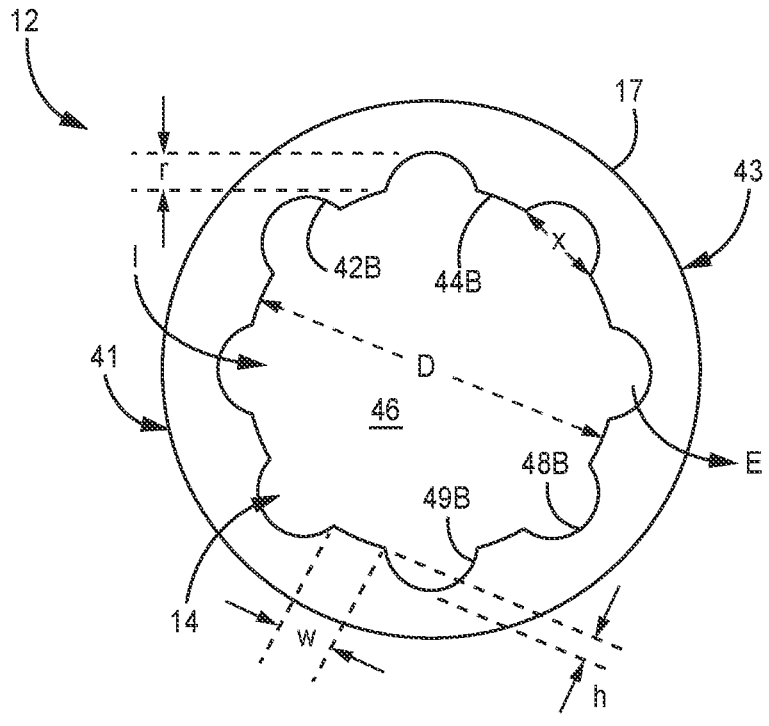

Referring now to FIGS. 1 and 2A-2B, the catheter body 12 further includes an internal fluid transport system 40 that can be used to inflate and deflate the balloon 30 when a fluid is delivered into the fluid ingress port 18 and flows out of the fluid egress ports 24, 26, or is withdrawn therefrom. The fluid transport system 40 includes an arrangement 41 with a plurality of structures 42 extending away from the internal surface 19 of the catheter body 12 and into the bore 14. In various embodiments, the structures 42 may be formed integrally with the catheter body 12 or may be formed as a separate unit or insert for placement in the bore 14. In various embodiments, the structures 42 may be formed from the same or a different polymeric material than the catheter body 12.

In the example embodiments shown in FIGS. 2A-2B, which are not intended to be limiting, the structures 42A can have a rectangular cross-sectional shape when viewed down the bore 14 and along the direction of arrow A in FIG. 1. The structures 42B have a generally trapezoidal cross-sectional shape, but in various embodiments the structures 42 could have cross-sectional shapes including triangular, pyramidal, semicircle, I-beam, and the like. The structures can include walls that are substantially straight, or are arcuate. While the embodiments in FIGS. 2A-2B show that the arrangement of structures 41 includes a plurality of substantially similar structures 42A, 42B, in some embodiments, the structures 42 in an arrangement 41 can have different shapes. In various examples, the structures may be present on all or a portion of the interior surface 19 of the catheter body 12 along the length of the bore 14, and may occupy all or a portion of a circumference of the interior surface 19. In various embodiments, the structures 42A, 42B may be integrally formed with the interior surface 19, or may be formed as an insert for placement in the bore 40 of the catheter 12.

In various embodiments, which are not intended to be limiting, the structures 42A-B have a height h of about 0.1 mm to about 5 mm, or about 1 mm to about 3 mm, or about 1 mm to about 1.5 mm, or about 1 mm to about 1.25 mm, above the internal surface 19. In various non-limiting embodiments, the structures 42A-B have widths w of about 0.1 mm to about 5 mm, or about 0.5 mm to about 2 mm, about 0.8 mm to about 1 mm. In various embodiments, the number of structures 42A-B present along the internal surface 19 can be 1 to 10, or 2 to 8, or 4 to 8. In some examples, a plurality of small structures 42A-B can be present to form a roughened internal surface 19, with the structures allowing fluid flow and circulation therebetween.

The structures 42A-B have exposed probe guide surfaces 44A-B, which form a lumen 46 therebetween. In some embodiments, the lumen 46 extends along the bore 14 from the proximal end 13 to the distal end 15 of the catheter body 12, and is configured to accept a small ultrasonic probe or array of probes such as, for example, a probe sized for use in intracardiac echo (ICE) imaging procedures. In various embodiments, the probe guide surfaces 44 may be configured to slideably receive and stabilize a selected ICE probe configuration so that the ICE probe can be more efficiently linearly and rotationally translated within the lumen 46. For example, in some embodiments the probe guide surfaces 44A-B may be concave (FIG. 2A) or substantially flat (FIG. 2B). In various examples, which are not intended to be limiting, the lumen 46 is configured to accept and allow linear translation and rotation of a probe with a diameter of about 3 mm to about 6 mm. For example, in various embodiments the lumen 46 has a diameter D of less than about 15 Fr (5 mm), or less than about 12 Fr (4 mm), or less than 10 Fr (3.3 mm), or even less than about 8 Fr (2.7 mm).

An arrangement 43 of elongate fluid channels 48A-B are interspersed with the structures 42A-B. One or more of the fluid channels 48A-B are in fluid communication with the lumen 46 and transport a fluid (not shown in FIG. 1 or 2A-2B) along an ingress direction I between the fluid ingress port 18 and the fluid egress port(s) 24, 26 to at least partially inflate or deflate the balloon 30. One or more of the elongate fluid channels 48A-B can also be used to evacuate air from the lumen 46 or the balloon 30 along an egress direction E during inflation or deflation procedures.

In various embodiments, the fluid channels 48A have a generally trapezoidal cross-sectional shape, while the fluid channels 48B have a generally arcuate or hemispherical shape when viewed in cross-section. However, like the structures 42A-B, in various embodiments the fluid channels 48A-B could have cross-sectional shapes including triangular, pyramidal, and the like. While the embodiments in FIGS. 2A-2B shown that the arrangement of fluid channels 43 have a plurality of substantially similar structures 42A-B, in some embodiments, the fluid channels within an arrangement 43 can have different shapes. In various examples, the fluid channels 48A-B may be present on all or a portion of the interior surface 19 of the catheter body 12 along the length of the bore 14, and may occupy all or a portion of a circumference of the interior surface 19.

In various embodiments, the fluid channels 48A-B have a depth r below the probe guide surfaces 44A-44B, or about 0.5 mm to about 5 mm, or about 1 mm to about 2 mm, or about 1 mm to about 1.5 mm. In various embodiments, the fluid channels 48A-B have widths x of about 0.1 mm to about 5 mm, or about 0.2 mm to about 1.5 mm, or about 0.2 mm to about 1.25 mm. In various embodiments, the fluid channels 48A-B include walls 49A-B that may be generally normal to the external surface 19 of the exterior surface 19 of the catheter body 12, or may be arcuate. In various embodiments, which are not intended to be limiting, the number of fluid channels 48A-B present can be 1 to 10, or 2 to 8, or 4 to 8.

Figure 2C:
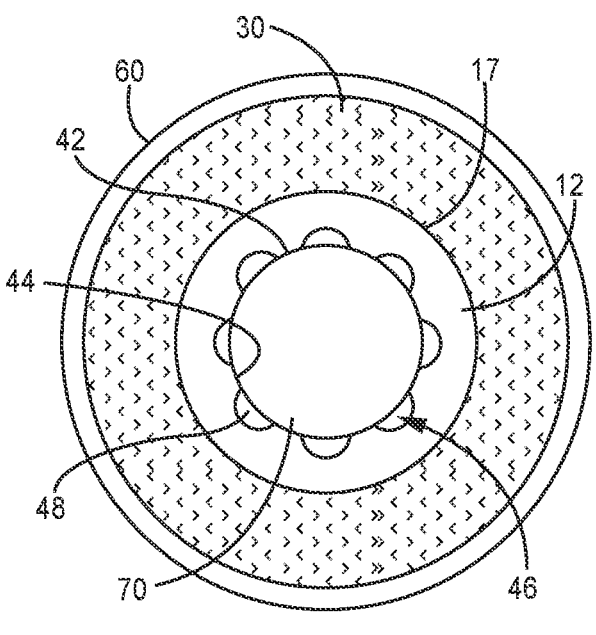
FIGS. 2C-2D are schematic cross-sectional views along the direction of arrow A of FIG. 1 of embodiments of balloon configurations in the catheter of FIG. 1 when the catheter is in an esophagus of a patient, and an ultrasonic probe is in the catheter.

Referring now to FIG. 2C, in some examples the balloon 30 extends around the full circumference of the tubular catheter body 12. When placed in an esophagus 60 of a patient, the balloon 30 can be filled with a fluid via the fluid channels 48 and expanded to fill symmetrically in the esophagus 60. An ultrasonic probe 70 such as, for example, an ICE probe, may be slidably and rotatably inserted into the lumen 46 and contacts the probe guide surfaces 44 on the structures 42.

Figure 2D:
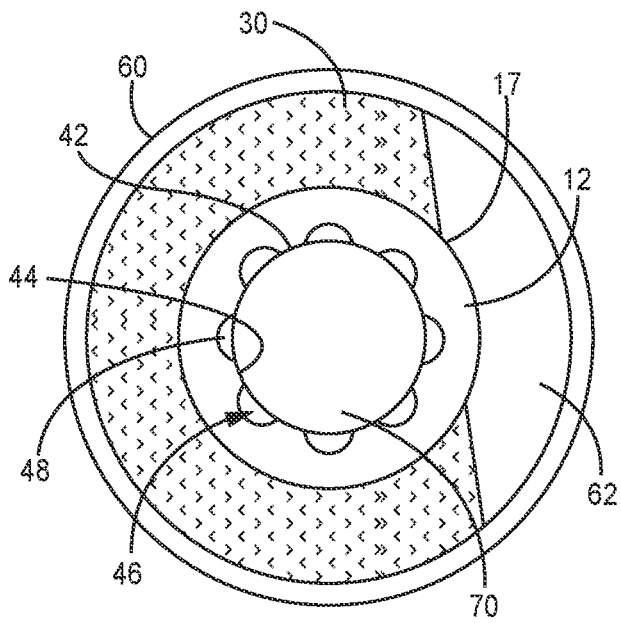

In another embodiment shown in FIG. 2D, the balloon 30 extends only a portion of the way around the circumference of the tubular catheter body 12. When placed in an esophagus 60 of a patient, the balloon 30 can be filled with a fluid via the fluid channels 48 and expanded to fill a portion of the esophagus 60, while leaving an unoccluded esophageal region 62 for saliva passage. A probe 70 may be slideably inserted into the lumen 46 and contacts the probe guide surfaces 44 on the structures 42.

Referring now to the schematic diagrams in FIGS. 3A-3B, in use the catheter 10 shown in detail in FIGS. 1 and 2A-2D above may be inserted into nasal passages of a patient and advanced into a passage 64 in the esophagus 60 of the patient. The catheter body 12 may be advanced along the esophageal wall 66 to an appropriate position to obtain an image of a region of a target tissue (not shown) including, but not limited to, cardiac tissue, vascular tissue, or retrosternal tissue, and the like. A fluid suitable for a desired ultrasonic imaging procedure, which in various embodiments may be an ultrasonically transparent fluid such as water or saline, a non-ultrasonically transparent fluid such as a radio-opaque contrast medium, or a mixture or combination thereof, may be introduced into the fluid ingress port (not shown in FIGS. 3A-3B, please see example in FIG. 1).

The fluid flows through the fluid channels and the working lumen 46 formed by the structures within the bore of the catheter body 12 and inflates the balloon 30. The walls 32 of the inflated balloon 30 contact the walls 66 of the esophagus 60 and form a conformal interface 68 therewith.

A suitably sized ultrasonic probe apparatus 70 such as, for example, an intracardiac echo (ICE) probe, can be inserted into the lumen 46 formed within the catheter body 12. The ultrasonic probe apparatus 70 includes a shaft 72, optionally containing pull wires, that can be manipulated manually or robotically to translate linearly and rotationally a transducer stack 74 including one or more transducers 76 into a desired position in the esophagus 60. The transducers 76 are maneuvered within the esophagus to reside within an imaging region 82 bounded by the conformal interface 68 formed by the walls 32 of the balloon 30. Since the probe apparatus 70 is small and flexible, the probe guide surfaces bounding the lumen 46 provide stability and precise guidance as the transducer stack 74 is linearly translated and rotated into a desired position. In various embodiments, which are not intended to be limiting, suitable probe apparatus include ultrasonic probes available from General Electric (GE), Philips, Siemens and the like.

The enhanced stability provided by the catheter 12 can in some cases allow a surgeon to easily maneuver and securely anchor the transducer stack 74 into position, which can potentially eliminate the need for multiple users to perform the imaging procedure, and reduce per-procedure costs. In some embodiments, the catheter 12 can optionally include additional features to assist in transducer stack placement such as, for example, guide wires, braids, coils and the like.

In various embodiments, which are provided by way of example, the transducers 76 operate over a frequency range of about 1 MHz to about 60 MHz, or about 3 MHz to about 10 MHz for transesophageal imaging procedures. In some examples, suitable transducers 76 have a focal length of about 1 cm to about 4 cm, or about 2 cm to about 3 cm. A transmission line (not shown in FIGS. 3A-3B) electrically connects the transducer stack 74 to control electronics (not shown in FIGS. 3A-3B, please see below). The transducers 76 emit an ultrasonic signal 80 within the imaging region 82 toward a target tissue 90. The conformal interface 68 within the imaging region 82 formed by the balloon 30 reduces or eliminates air gaps along the path of the ultrasonic signal 80, which can reduce shadowing effects in an ultrasonic image of the target tissue 90. The enlarged imaging region 82 also provides a wider field of view for the transducers 76.

For example, if there is an airgap adjacent to a part of the transducer 76, the observer will only be able to utilize a portion of the field of view, and the other part is blocked by air. By eliminating the air gap, the useful field of view of effectively increased.

In addition, ultrasound images typically (though not always) are created in such a way that they fan out as they go deeper, and the field of view becomes bigger/wider at deeper depths. By incorporating the balloon 30 on the distal end of the catheter 12, the ultrasonic probe 76 is effectively retracted from the esophagus by a small offset amount (for example, by about 1 cm). Therefore, the tissue to be imaged is deeper by the offset amount than when imaged with a probe 76 resting against a wall of the esophagus. Because the tissue to be imaged is deeper, your field of view becomes a bit wider, which enables a more expansive view.

Figure 4A:
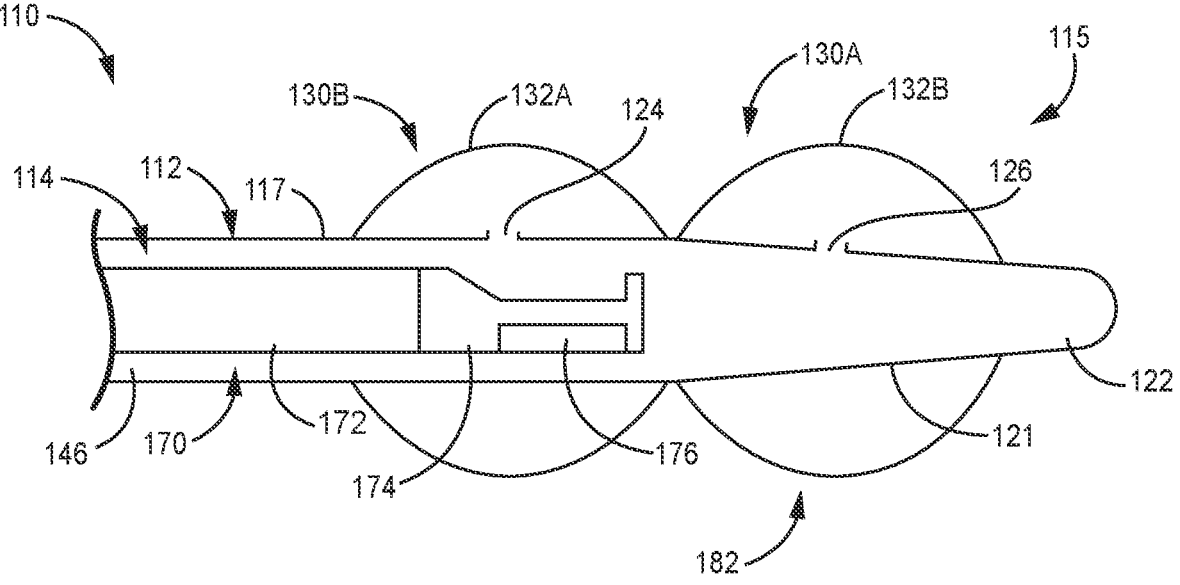
FIG. 4A is a schematic cross-sectional view of an embodiment of a catheter of the present disclosure including a catheter body with a tapered distal and an atraumatic tip.

Referring now to the schematic depiction in FIG. 4A, in an alternative embodiment a distal end 115 of a catheter 110 includes a catheter body 112 having a tapering region 121 and a closed tip 122. The tapering region 121 works in combination with an atraumatic tip 122 having a dilating shape to ease insertion into a nasal passage and an esophagus of a patient. As noted above, in some embodiments the atraumatic tip 122 can be made of a polymeric material that is softer and more compliant than the polymeric material of the catheter body 112. The tip 122 can be formed integrally with the catheter body 112, or can be molded separately and attached to the catheter body 112 by any suitable technique.

The catheter 110 also includes a plurality of balloons 130A-130B, each having a respective wall 132A, 132B bonded with an outer surface 117 of the catheter body 112. The balloons 130A, 130B are inflated and deflated via fluid flow through respective fluid egress ports 124, 126.

A longitudinal bore 114 within the catheter body 112 includes an arrangement of projections (not shown in FIG. 4A) as described above to form a working lumen 146 for linearly translating and rotating a catheter shaft 172 to precisely position an ultrasonic imaging apparatus 170 such as, for example, an ICE probe. Fluid channels (not shown in FIG. 4A) interspersed with the projections supply a fluid to fluid egress ports 124, 126 to inflate and deflate the balloons 130A, 130B.

The multiple balloons 130A, 130B can provide a larger imaging region 182 and improved tissue contact when the balloons 130A, 130B contact an esophageal wall to form a conformal interface therewith. The large conformal interface formed by the balloons 130A, 130B efficiently provides a large acoustic window to provide transmission of signals to and from a transducer 176 in a transducer stack 174.

Figure 4B:
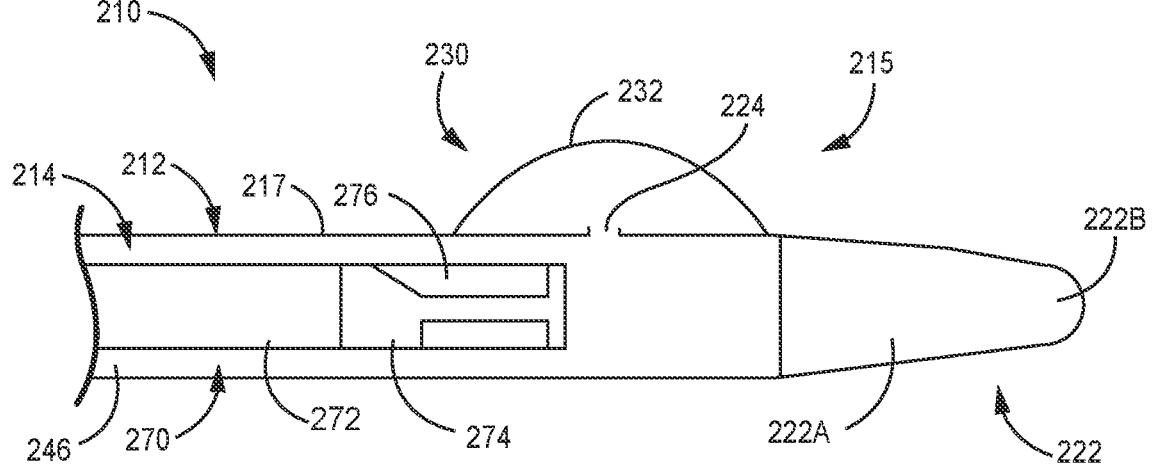
FIG. 4B is a schematic cross-sectional view of an embodiment of a catheter of the present disclosure including a tapered atraumatic dilating tip.

Referring now to another embodiment shown in the schematic depiction in FIG. 4B, a distal end 215 of a catheter 210 includes a catheter body 212 having a closed tip 222. The tip 222 includes a tapering region 222A and an atraumatic dilation region 222B. The tip 222 eases insertion of the catheter 210 into a nasal passage and an esophagus of a patient. As noted above, in some embodiments either or both portions of the tip 222 can be made of a polymeric material that is softer and more compliant than the polymeric material of the catheter body 212. The tip 222 can be formed integrally with the catheter body 212, or can be molded separately and attached to the catheter body 212 by any suitable technique.

The catheter 210 also includes a balloon 230 with a wall 232 bonded with an outer surface 217 of the catheter body 212. The balloon 230 is inflated and deflated via fluid flow through a fluid egress port 224.

A longitudinal bore 214 within the catheter body 212 includes an arrangement of projections (not shown in FIG. 4B) as described above to form a working lumen 246 for linearly translating and rotating a catheter shaft 272 to precisely position an ultrasonic imaging apparatus 270 such as, for example, an ICE probe. Fluid channels (not shown in FIG. 4B) interspersed with the projections supply a fluid to the fluid egress ports 224 to inflate and deflate the balloon 230.

A large conformal interface formed by the balloon 230 efficiently provides a large acoustic window to provide transmission of signals to and from a transducer 276 in a transducer stack 274.

Figure 5:
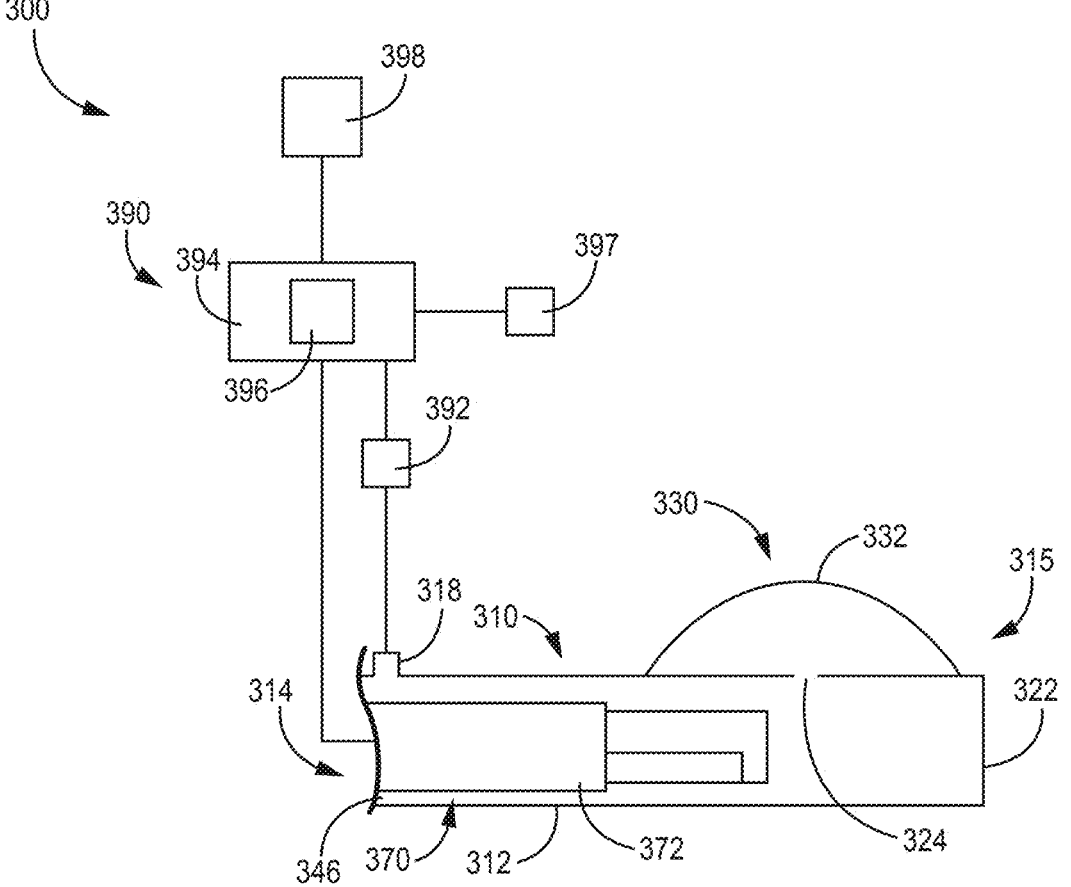
FIG. 5 is a schematic diagram of an embodiment of an imaging system incorporating the catheter of the present disclosure.

Referring now to FIG. 5, a schematic diagram of an example embodiment of a system 300 includes a catheter 310 having a catheter body 312 and a closed tip 322. A distal end 315 of the catheter 310 includes a balloon 330 having a body 332 attached to an outer surface 317 of the catheter body 312. The balloon 330 is inflated and deflated by a fluid delivered to a fluid ingress port 318, which is supplied through a network of fluid channels as described above (not shown in FIG. 5) in a longitudinal bore 314 of the catheter body 312 to a fluid egress port 324.

The longitudinal bore 314 within the catheter body 312 includes an arrangement of projections (not shown in FIG. 5) as described above to form a working lumen 346 for linearly translating and rotating a catheter shaft 372 to precisely position an ultrasonic imaging apparatus 370 such as, for example, an ICE probe.

In some embodiments, the system 300 includes a controller or patient interface module 390. The catheter body 312 can be manually manipulated by a user, or in some examples the patient interface module 390 is configured to automatically control various functions of the movement of the ultrasonic imaging apparatus 370 within the working lumen 346 of the catheter 312. For example, the patient interface module 390 may be configured to control at least one of linear translation or rotation of the ultrasonic imaging apparatus 370 via the catheter shaft 372. In another embodiment, the imaging apparatus 370 may include an optical system to view the position of the ICE probe in an esophagus of a patient, and the patient interface module 390 may be configured to control or capture and process images from the optical system. In another embodiment, the patient interface module 390 may be configured to control a fluid supply system 392 including suitable fluid pumps, reservoirs, temperature and pressure sensors, and the like.

The patient interface module 390 includes a processor 396 in a computing device 394 to process signals from the imaging apparatus 370 and the fluid supply system 392. In various embodiments, the processor 396 may be integrated with the imaging apparatus 370 or the fluid supply system 392, or may be a remote processor.

The processor 396 in the computing device 394 may be any suitable software, firmware, hardware, or combination thereof. The processor 396 may include any one or more microprocessors, controllers, digital signal processors (DSPs), application specific integrated circuits (ASICs), field-programmable gate arrays (FPGAs), or discrete logic circuitry. The functions attributed to the processor 396 may be provided by processing circuitry of a hardware device, e.g., as supported by software and/or firmware.

In some examples, the processor 396 may be coupled to memory 397, which may be part of the computing device 394 or remote thereto. The memory 397 may include any volatile or non-volatile media, such as a random-access memory (RAM), read only memory (ROM), non-volatile RAM (NVRAM), electrically erasable programmable ROM (EEPROM), flash memory, and the like. The memory 397 may be a storage device or other non-transitory medium. The memory 397 may be used by the processor 396 to, for example, store imaging data pertinent to an ultrasonic scanning procedure, or other patient information for retrieval during or after the imaging procedure.

In some embodiments, the processor 396 is coupled to user interface 398, which may include a display, user input, and output, and the like (not shown in FIG. 5). Suitable display devices include, for example, monitor, PDA, mobile phone, tablet computers, and the like. In some examples, user input may include components for interaction with a user, such as a keypad and a display such as a cathode ray tube (CRT) display, a liquid crystal display (LCD) or light emitting diode (LED) display, and the keypad may take the form of an alphanumeric keypad or a reduced set of keys associated with particular functions. In some examples, the displays may include a touch screen display, and a user may interact with user input via the touch screens of the displays.

In some examples, the user may also interact with the user input remotely via a networked computing device.

In some embodiments, the patient interface module 390 can include a controller 394 that generates control signals for, for example, linear translation or rotation of the ultrasonic imaging apparatus 370, the fluid pressure in the fluid supply system 392, and the like. The controller 394 may be adjusted by a variety of manual and automatic means. Automatic means may make use of any number of control algorithms such as, for example, adaptive algorithms such as so-called "machine-learning" algorithms. In some embodiments, the controller 394 can utilize information from other sources such as, for example, infrared cameras, previous imaging data, and the like, to determine the control action decided by algorithms or machine learning schemes.

In another embodiment shown in the flow chart of FIG. 6, the present disclosure is directed to a method 400 for imaging a target tissue.

The method 400 includes inserting a balloon catheter into an esophageal region of a patent (402). The balloon catheter includes a distal end with a closed tip and at least one compliant balloon, wherein a bore of the catheter body includes an arrangement of structures with exposed probe guide surfaces that form a lumen with a diameter of less than about 15 Fr (5 mm). The method 400 includes inserting a fluid into an arrangement of elongate fluid channels between the structures, wherein the fluid channels are in fluid communication with the lumen and transport a fluid to sufficiently inflate the balloon to form a conformal interface with a selected region of esophageal wall tissue (404).

The method 400 includes providing an ultrasonic probe in the lumen, and linearly translating and rotating the probe in the lumen to establish an acoustic window between a transducer on the probe and a target region of tissue to be imaged with the probe (406).

In some embodiments, the balloon catheter is first inserted into the nasal passages of a patent, manipulated into a desired position in the esophagus of the patient, and the ultrasonic probe is then inserted into the catheter and moved into position within the catheter lumen to a preferred viewing location. The catheter may include optional braids, coils, wires and the like to improve overall stiffness and enable more precise positioning in the esophagus. In some embodiments, the catheter may also be used with an optional introducer or dilator to ease movement through the nasal passages and esophagus of the patient.

In some embodiments, the ultrasonic probe is first inserted into the catheter lumen before the catheter lumen is inserted into the nasal passages of the patient, and the catheter and probe are then manipulated together through the patient anatomy to a preferred viewing position. In some examples, the optional dilator or introducer may be used to navigate the anatomy of the patient, or the catheter may be reinforced with braids, coils, and the like to get shaft mechanics that can be pushed through anatomy and torqued to move the system to a preferred viewing position.

In an exemplary TNTEE imaging procedure using the catheter of the present disclosure in combination with an ICE probe, ultrasound images can be obtained of the internal heart chambers such as the left atrium. Sufficient contact and improved near field of view may facilitate overall visualization of other heart structures, such as all four pulmonary veins entering the left atrium. In some embodiments, the improved field of view provided by the catheter of the present disclosure may be used in guiding ablation therapy procedures in the pulmonary veins, on the interatrial septum and the like.

In some additional examples, which are not intended to be limiting, the catheter of the present disclosure may be used to visualize patient anatomy in the delivery of implantable medical devices such as leads, valves, leadless pacemakers, cardiac closure devices, and the like. The catheter may be used to deliver the implantable medical devices not only to the left atrium, but also into the left ventricle (examples: mitral valve, aortic valve, left ventricular assist device), the right atrium (examples: right atrial cardiac pacing lead, leadless pacemaker), and right ventricle (examples: defibrillator lead, leadless pacemaker). Anatomy that could be visualized with the catheters of the present disclosure to deliver implantable medical devices include, but are not limited to, the superior vena cava (SVC), inferior vena cava (IVC), tricuspid valve, mitral valve, aortic valve, pulmonary valve, interatrial septum, interventricular septum, coronary sinus, foramen ovale, fossa ovalis, left atrial appendage, and right atrial appendage.

EMBODIMENTS

Embodiment A. A transnasal transesophogeal balloon catheter, comprising:

an elongate flexible tubular body with an internal surface, an external surface, and a bore extending from a proximal end to a distal end thereof, wherein the proximal end of the tubular body comprises a valve for introduction of an ultrasound probe and a fluid ingress port, and a distal end of the tubular body comprises a closed tip and a fluid egress port, wherein the fluid egress port is fluidly connected to at least one compliant balloon attached to the external surface of the tubular body, and wherein at least one balloon overlies an imaging region of the tubular body;

an arrangement of structures extending away from the internal surface of the tubular body and into the bore, wherein exposed probe guide surfaces on the structures form a lumen with a diameter of less than about 15 French (Fr) (5 mm) extending from the proximal end to the distal end of the tubular body and configured to slidably and rotatably receive the ultrasound probe; and an arrangement of elongate fluid channels interspersed with the structures, wherein the fluid channels are in fluid communication with the lumen and transport a fluid between the fluid ingress port and the fluid egress port to at least partially inflate or deflate the balloon.

Embodiment B. The catheter of Embodiment A, wherein the balloon is configured to be inflatable in the imaging region to form a conformal interface with a selected region of esophageal wall tissue and provide a substantially air-free path between a transducer on the ultrasound probe and a target region of tissue to be imaged with the ultrasound probe.

Embodiment C. The catheter of Embodiments A or B, wherein the lumen is configured to accept an intracardiac echo probe.

Embodiment D. The catheter of any of Embodiments A to C, wherein the lumen has a diameter of less than about 12 Fr (4 mm).

Embodiment E. The catheter of any of Embodiments A to D, wherein the lumen has a diameter of less than about 10 Fr (3.3 mm).

Embodiment F. The catheter of any of Embodiments A to E, wherein the structures have a trapezoidal cross-sectional shape and the fluid channels have a hemispherical cross-sectional shape when viewed down the bore of the tubular body along a longitudinal axis thereof.

Embodiment G. The catheter of Embodiment F, wherein the probe guide surfaces are substantially flat.

Embodiment H. The catheter of Embodiment F or G, wherein the probe guide surfaces are concave.

Embodiment I. The catheter of any of Embodiments A to H, wherein the structures have a rectangular cross-sectional shape and the fluid channels have a trapezoidal cross-sectional shape when viewed down the bore of the tubular body along a longitudinal axis thereof.

Embodiment J. The catheter of Embodiment I, wherein the probe guide surfaces on the structures are concave.

Embodiment K. The catheter of any of Embodiments A to J, wherein the probe guide surfaces have a height of about 0.5 mm to about 5 mm above the internal surface of the tubular body.

Embodiment L. The catheter of any of Embodiments A to K, wherein the fluid channels have a depth of about 0.5 mm to about 5 mm below the probe guide surfaces on the structures.

Embodiment M. The catheter of any of Embodiments A to L, wherein the tip of the tubular body has an atraumatic shape.

Embodiment N. The catheter of Embodiment M, wherein the tip of the tubular body has a dilating shape.

Embodiment O. The catheter of Embodiments M or N, wherein the tip of the tubular body is tapered.

Embodiment P. The catheter of any of Embodiments A to O, wherein the tip is integral with the tubular body.

Embodiment Q. The catheter of any of Embodiments A to P, wherein the tubular body comprises a first polymeric material, and the tip comprises a second polymeric material different from the first polymeric material.

Embodiment R. The catheter of any of Embodiments A to Q, wherein the fluid is ultrasonically transparent.

Embodiment S. The catheter of Embodiment R, wherein the fluid comprises water, saline, and mixtures and combinations thereof.

Embodiment T. The catheter of any of Embodiments A to S, wherein the lumen and the fluid channels form a fluid transport network within the catheter body such that the ultrasound probe is free of contact with a bodily fluid during an imaging procedure.

Embodiment U. The catheter of any of Embodiments A to T, wherein the balloon has a length of about 2 cm to about 10 cm, and an inflated diameter of about 2 cm to about 4 cm.

Embodiment V. The catheter of any of Embodiments A to U, wherein the balloon extends around a circumference of the external surface of the tubular body.

Embodiment W. The catheter of any of Embodiments A to V, wherein the balloon extends around a portion of a circumference of the external surface of the tubular body, and wherein the portion of the circumference is less than the entire circumference.

Embodiment X. The catheter of any of Embodiments A to W, wherein the catheter comprises a plurality of balloons.

Embodiment Y. The catheter of any of Embodiments A to X, wherein the tubular body comprises a compliant polymeric material chosen from polyethylene (PE), nylon, silicone, polyurethane, polyether block amide, and combinations thereof.

Embodiment Z. The catheter of any of Embodiments A to Y, wherein the balloon comprises a polymeric material chosen from polyethylene (PE), ethylene vinyl alcohol (EVA), silicone, polyurethane, polyether block amide, and mixtures and combinations thereof.

Embodiment AA. The catheter of any of Embodiments A to Z, wherein the tubular body comprises a plurality of layers of polymeric materials.

Embodiment BB. The catheter of any of Embodiments A to AA, wherein the tubular body comprises a metal reinforcing material.

Embodiment CC. The catheter of any of Embodiments A to BB, wherein at least one of the tubular body and the balloon comprise an ultrasound enhancing structure.

Embodiment DD. The catheter of any of Embodiments A to CC, wherein the structures comprise a first polymeric material and the tubular body comprises a second polymeric material different from the first polymeric material.

Embodiment EE. The catheter of any of Embodiments A to DD, wherein the catheter body further comprises a braid, a coil, and combinations thereof.

Embodiment FF. The catheter of any of Embodiments A to EE, wherein the catheter body further comprises a pull wire.

Embodiment GG. A system, comprising:
    a balloon catheter, comprising:
        an elongate flexible tubular body with an internal surface, an external surface, and an open bore extending from a proximal end to a distal end thereof, wherein the proximal end of the tubular body comprises a valve configured to sealably accept an ultrasound probe and a fluid ingress port, and a distal end of the tubular body comprises a closed tip and a fluid egress port, wherein the fluid egress port is fluidly connected to at least one compliant balloon attached to the external surface of the tubular body, and wherein the at least one balloon overlies an imaging region of the tubular body;
        an arrangement of structures extending away from the internal surface of the tubular body and into the bore, wherein exposed probe guide surfaces on the structures form a lumen with a diameter of less than about 15 Fr (5 mm) extending from the proximal end to the distal end of the tubular body and configured to slidably receive the ultrasound probe; and
        an arrangement of elongate fluid channels between the structures, wherein the fluid channels are in fluid communication with lumen and transport a fluid between the fluid ingress port and the fluid egress port to at least partially inflate or deflate the balloon in the imaging region; and
        an intracardiac echo probe in the lumen, wherein the probe is linearly translatable and rotatable in the lumen.

Embodiment HH. The system of Embodiment GG, wherein the balloon is sufficiently inflatable in the imaging region to form a conformal interface with a selected region of esophageal wall tissue and provide a substantially air-free path between a transducer on the probe and a target region of tissue to be imaged with the probe.

Embodiment II. The system of any of Embodiments GG to HH, further comprising a controller to provide at least one of linear translation and rotation of the probe in the lumen.

Embodiment JJ. The system of any of Embodiments GG to II, further comprising at least one display module to display an image of the target tissue.

Embodiment KK. The system of Embodiment JJ, wherein the target tissue is cardiac tissue, vascular tissue, or retrosternal tissue.

Embodiment LL. A method for ultrasonic imaging a target tissue, the method comprising:

inserting a balloon catheter into an esophageal region, wherein the balloon catheter comprises:

an elongate flexible tubular body with an internal surface, an external surface, and an open bore extending from a proximal end to a distal end thereof, wherein the proximal end of the tubular body comprises a valve configured for sealable introduction of an intracardiac echo probe and a fluid ingress port, and a distal end of the tubular body comprises a closed tip and a fluid egress port, wherein the fluid egress port is fluidly connected to at least one compliant balloon attached to the external surface of the tubular body, and wherein the at least one balloon overlies an imaging region of the tubular body;

an arrangement of structures extending away from the internal surface of the tubular body and into the bore, wherein exposed probe guide surfaces on the structures form a lumen with a diameter of less than about 15 Fr (5 mm) extending from the proximal end to the distal end of the tubular body and configured to slidably and rotatably receive the probe; and an arrangement of elongate fluid channels between the structures, wherein the fluid channels are in fluid communication with lumen and transport a fluid between the fluid ingress port and the fluid egress;

linearly translating and rotating the balloon catheter to a selected region of esophageal wall tissue; and inserting a fluid into the fluid ingress port such that the fluid enters the fluid channels and the lumen and flows from the liquid egress port to sufficiently inflate the balloon in the imaging region to form a conformal interface with the selected region.

Embodiment MM. The method of Embodiment LL, wherein the balloon catheter is inserted into a nasogastric region prior to insertion into the esophageal region.

Embodiment NN. The method of Embodiments LL or MM, further comprising inserting an intracardiac echo probe into the lumen of the catheter to establish an acoustic window between a transducer on the probe and the selected target tissue to be imaged with the probe.

Embodiment OO. The method of Embodiment NN, wherein the probe is inserted into the lumen of the catheter prior to insertion of the catheter into the nasogastric region.

Embodiment PP. The method of Embodiment NN, wherein the probe is inserted into the lumen of the catheter after the catheter is positioned in the selected region of esophageal wall tissue.

Embodiment QQ. The method of any of Embodiments LL to PP, wherein the target tissue is a cardiac tissue, vascular tissue, or retrosternal tissue.

Embodiment RR. The method of any of Embodiments LL to QQ, wherein the closed end of the tubular body comprises an atraumatic tip with a tapered dilating profile.

Embodiment SS. The method of any of Embodiments LL to RR, wherein the fluid is ultrasonically transparent.

Embodiment TT. The method of any of Embodiments LL to SS, further comprising delivering an implantable medical device to the selected target tissue.

Various embodiments of the invention have been described. These and other embodiments are within the scope of the following claims.

The invention claimed is:

1. A transnasal transesophogeal balloon catheter, comprising:

an elongate flexible tubular body with an internal surface, an external surface, and a bore extending from a proximal end to a distal end thereof, wherein the proximal end of the tubular body comprises a valve for introduction of an ultrasound probe and a fluid ingress port, and a distal end of the tubular body comprises a closed tip and a fluid egress port;

at least one balloon attached to the external surface of the tubular body, wherein the at least one balloon is proximal to the closed tip and is fluidly connected to the fluid egress port, wherein the at least one balloon overlies an imaging region of the tubular body, wherein the least one balloon extends around a portion of a circumference of the external surface of the tubular body so that, when inflated, the least one balloon is configured to fill a first esophageal region to provide a substantially air-free path between a transducer on the ultrasound probe and a target region of tissue to be imaged with the ultrasound probe, and wherein the portion of the circumference is less than the entire circumference so that, when inflated, the least one balloon is configured to leave a second esophageal region unoccluded for saliva passage;

an arrangement of structures extending away from the internal surface of the tubular body and into the bore, wherein exposed probe guide surfaces on the structures form a lumen with a diameter of less than about 15 French (Fr) (5 mm) extending from the proximal end to the distal end of the tubular body and configured to slidably and rotatably receive the ultrasound probe; and an arrangement of elongate fluid channels interspersed with the structures, wherein the fluid channels are in fluid communication with the lumen and transport a fluid between the fluid ingress port and the fluid egress port to at least partially inflate or deflate the at least one balloon.

2. The catheter of claim 1, wherein the lumen is configured to accept an intracardiac echo probe.

3. The catheter of claim 1, wherein the lumen has a diameter of less than about 12 Fr (4 mm).

4. The catheter of claim 1, wherein the structures have a trapezoidal cross-sectional shape and the fluid channels have a hemispherical cross-sectional shape when viewed down the bore of the tubular body along a longitudinal axis thereof.

5. The catheter of claim 4, wherein the probe guide surfaces are substantially flat or concave.

6. The catheter of claim 1, wherein the structures have a rectangular cross-sectional shape and the fluid channels have a trapezoidal cross-sectional shape when viewed down the bore of the tubular body along a longitudinal axis thereof.

7. The catheter of claim 6, wherein the probe guide surfaces on the structures are concave.

8. The catheter of claim 1, wherein the lumen and the fluid channels form a fluid transport network within the catheter body such that the ultrasound probe is free of contact with a bodily fluid during an imaging procedure.

9. The catheter of claim 1, wherein at least one of the tubular body and the at least one balloon comprise an ultrasound enhancing structure.

10. A system, comprising:
a balloon catheter, comprising:
    an elongate flexible tubular body with an internal surface, an external surface, and an open bore extending from a proximal end to a distal end thereof, wherein the proximal end of the tubular body comprises a valve configured to sealably accept an ultrasound probe and a fluid ingress port, and a distal end of the tubular body comprises a closed tip and a fluid egress port;
    at least one balloon attached to the external surface of the tubular body, wherein the at least one balloon is proximal to the closed tip and is fluidly connected to the fluid egress port, wherein the at least one balloon overlies an imaging region of the tubular body, wherein the least one balloon extends around a portion of a circumference of the external surface of the tubular body so that, when inflated, the least one balloon is configured to fill a first esophageal region to provide a substantially air-free path between a transducer on the ultrasound probe and a target region of tissue to be imaged with the ultrasound probe, and wherein the portion of the circumference is less than the entire circumference so that, when inflated, the least one balloon is configured to leave a second esophageal region unoccluded for saliva passage;
    an arrangement of structures extending away from the internal surface of the tubular body and into the bore, wherein exposed probe guide surfaces on the structures form a lumen with a diameter of less than about 15 Fr (5 mm) extending from the proximal end to the distal end of the tubular body and configured to slidably receive the ultrasound probe; and
    an arrangement of elongate fluid channels between the structures, wherein the fluid channels are in fluid communication with lumen and transport a fluid between the fluid ingress port and the fluid egress port to at least partially inflate or deflate the at least one balloon in the imaging region; and
    an intracardiac echo probe in the lumen, wherein the probe is linearly translatable and rotatable in the lumen.

11. The system of claim 10, further comprising a controller to provide at least one of linear translation and rotation of the probe in the lumen.

12. A method for ultrasonic imaging a target tissue, the method comprising:

inserting a balloon catheter into an esophageal region, wherein the balloon catheter comprises:
    an elongate flexible tubular body with an internal surface, an external surface, and an open bore extending from a proximal end to a distal end thereof, wherein the proximal end of the tubular body comprises a valve configured for sealable introduction of an intracardiac echo probe and a fluid ingress port, and a distal end of the tubular body comprises a closed tip and a fluid egress port;
    at least one balloon attached to the external surface of the tubular body, wherein the at least one balloon is proximal to the closed tip and is fluidly connected to the fluid egress port, wherein the at least one balloon overlies an imaging region of the tubular body, wherein the least one balloon extends around a portion of a circumference of the external surface of the tubular body so that, when inflated, the least one balloon is configured to fill a first esophageal region to provide a substantially air-free path between a transducer on the ultrasound probe and a target region of tissue to be imaged with the ultrasound probe, and wherein the portion of the circumference is less than the entire circumference so that, when inflated, the least one balloon is configured to leave a second esophageal region unoccluded for saliva passage;
    an arrangement of structures extending away from the internal surface of the tubular body and into the bore, wherein exposed probe guide surfaces on the structures form a lumen with a diameter of less than about 15 Fr (5 mm) extending from the proximal end to the distal end of the tubular body and configured to slidably and rotatably receive the probe; and
    an arrangement of elongate fluid channels between the structures, wherein the fluid channels are in fluid communication with lumen and transport a fluid between the fluid ingress port and the fluid egress;
linearly translating and rotating the balloon catheter to a selected region of esophageal wall tissue; and
inserting a fluid into the fluid ingress port such that the fluid enters the fluid channels and the lumen and flows from the liquid egress port to sufficiently inflate the at least one balloon in the imaging region to form a conformal interface with the selected region.

13. The method of claim 12, wherein the balloon catheter is inserted into a nasogastric region prior to insertion into the esophageal region.

14. The method of claim 13, further comprising inserting an intracardiac echo probe into the lumen of the catheter to establish an acoustic window between a transducer on the probe and the selected target tissue to be imaged with the probe.

15. The method of claim 12, further comprising delivering an implantable medical device to the selected target tissue.

\* \* \* \* \*